United States Patent [19]

Yamamoto

[11] Patent Number: 5,326,749
[45] Date of Patent: * Jul. 5, 1994

[54] MACROPHAGE ACTIVATING FACTOR FROM VITAMIN D BINDING PROTEIN

[76] Inventor: Nobuto Yamamoto, 1040 66th Ave., Philadelphia, Pa. 19126

[*] Notice: The portion of the term of this patent subsequent to Aug. 31, 2010 has been disclaimed.

[21] Appl. No.: 320

[22] Filed: Jan. 4, 1993

Related U.S. Application Data

[63] Continuation-in-part of Ser. No. 767,742, Sep. 30, 1991, Pat. No. 5,177,001, and a continuation-in-part of Ser. No. 576,248, Aug. 31, 1990, Pat. No. 5,177,002, which is a continuation-in-part of Ser. No. 439,223, Nov. 20, 1989, abandoned.

[51] Int. Cl.$^5$ .............. A61K 37/02; C07K 7/10; C07K 9/00; C07K 15/14
[52] U.S. Cl. .................. 514/8; 530/362; 530/380; 530/395
[58] Field of Search ............ 514/8; 530/380, 395, 530/362

[56] References Cited

U.S. PATENT DOCUMENTS 5,177,001 1/1993 Yamamoto .................. 435/68.1
5,177,002 1/1993 Yamamoto .................. 435/68.1

OTHER PUBLICATIONS

Yamamoto et al., *Cancer Research* 47:2008, 1987.
Yamamoto et al., *Cancer Immunol. Immunother.* 25:185, 1987.
Yamamoto et al., *Cancer Res.* 48:6044, 1988.
Ngwenya et al., *Abstracts of the Annual Meeting of the American Society of Microbiology*, Abs. E-72, p. 121 (1988).
Homma, *Abstracts of the Annual Meeting of the Am. Society of Microbiology*, Abs. E-74, p. 121 (1988).
Cooke et al., *J. Clin. Invest.* 76:2420–2424 (1985).
Yang et al., *Proc. Natl. Acad. Sci.* 82:7994–7998 (1985).
Biological Abstracts 68(5) p. 2831 (1979) Abs. No. 28360.
Yamamoto, et al., *Proc. Natl. Acad. Sci. USA* 88, 8539–8543 (1991).
Haddad et al., *Biochem. J.* 218:805, 1984.
Link et al., *Analyt. Biochem.* 157: 262–269, 1986.
Cooke et al., *Endocrine Reviews* 10:294–307, 1989.
Ogata et al., *Comp. Biochem. Physiol.* 90B:193–199, 1988.
Van De Weghe et al., *Comp. Biochem. Physiol.* 73B977–982, 1982.
Van Baelen et al. *J. Biol. Chem.* 253:6344–6345, Sep. 25, 1978.
Svasti et al., *J. Biol. Chem.* 253:4188–4194, Jun. 25, 1978.
Shinomiya et al., *J. Biochem.* 92:1163–1171, 1982.
Gahne et al., *Anim. Blood Groups Biochem. Genet.* 9, 37–40 (1978).
Homma and Yamamoto, *Clin. Exp. Immunol.* 79, 307–313 (1990).
Homma et al., *Immunol. Cell. Biol.* 68, 137–142 (1990).
Yamamoto et al., *Immunology* 74, 420–424 (1991).
Yamamoto et al., *J. Immunol.* 147, 273–280 (Jul. 1, 1991).
Viau et al., "Isolation and characterization of the O-glycan chain of the human vitamin-D binding protein", *Bch. B Phys. Res. Comm.*, 117:324–331 (1983).
Coppenhaver et al., "Post-Translational Heterogeneity of the Human Vitamin D-Binding Protein", *Arch. Biochem. Biophys.* 226(1):218–223 (1983).
Schulz et al., *Principles of Protein Structure*, pp. 14–16 (1979).

*Primary Examiner*—Robert A. Wax
*Assistant Examiner*—Stephen G. Walsh
*Attorney, Agent, or Firm*—Seidel, Gonda, Lavorgna & Monaco

[57] ABSTRACT

A novel macrophage activating factor is prepared in vitro by treating glycosated vitamin D-binding protein with glycosidases. Vitamin D-binding protein, which is isolated from blood or plasma of mammals by known procedures, is thus readily converted to a highly potent macrophage activating factor.

4 Claims, 4 Drawing Sheets

```
                                        10
Leu Glu Arg Gly Arg Asp Tyr Glu Lys Asn Lys Val Cys Lys Glu
                20                                           30
Phe Ser His Leu Gly Lys Glu Asp Phe Thr Ser Leu Ser Leu Val
                                        40
Leu Tyr Ser Arg Lys Phe Pro Ser Gly Thr Phe Glu Gln Val Ser
                50                                           60
Gln Leu Val Lys Glu Val Val Ser Leu Thr Glu Ala Cys Cys Ala
                                        70
Glu Gly Ala Asp Pro Asp Cys Tyr Asp Thr Arg Thr Ser Ala Leu
                80                                           90
Ser Ala Lys Ser Cys Glu Ser Asn Ser Pro Phe Pro Val His Pro
                                       100
Gly Thr Ala Glu Cys Cys Thr Lys Glu Gly Leu Glu Arg Lys Leu
               110                                          120
Cys Met Ala Ala Leu Lys His Gln Pro Gln Glu Phe Pro Thr Tyr
                                       130
Val Glu Pro Thr Asn Asp Glu Ile Cys Glu Ala Phe Arg Lys Asp
               140                                          150
Pro Lys Glu Tyr Ala Asn Gln Phe Met Trp Glu Tyr Ser Thr Asn
                                       160
Tyr Glu Gln Ala Pro Leu Ser Leu Leu Val Ser Tyr Thr Lys Ser
               170                                          180
Tyr Leu Ser Met Val Gly Ser Cys Cys Thr Ser Ala Ser Pro Thr
                                       190
Val Cys Phe Leu Lys Glu Arg Leu Gln Leu Lys His Leu Ser Leu
               200                                          210
Leu Thr Thr Leu Ser Asn Arg Val Cys Ser Gln Tyr Ala Ala Tyr
                                       220
Gly Glu Lys Lys Ser Arg Leu Ser Asn Leu Ile Lys Leu Ala Gln
               230                                          240
Lys Val Pro Thr Ala Asp Leu Glu Asp Val Leu Pro Leu Ala Glu (Continued in Figure 1B)
```

FIGURE 1A (Continued from Figure 1A)

```
                                    250
Asp Ile Thr Asn Ile Leu Ser Lys Cys Cys Glu Ser Ala Ser Glu
                260                                     270
Asp Cys Met Ala Lys Glu Leu Pro Glu His Thr Val Lys Leu Cys
                                    280
Asp Asn Leu Ser Thr Lys Asn Ser Lys Phe Glu Asp Cys Cys Gln
                290                                     300
Glu Lys Thr Ala Met Asp Val Phe Val Cys Thr Tyr Phe Met Pro
                                    310
Ala Ala Gln Leu Pro Glu Leu Pro Asp Val Arg Leu Pro Thr Asn
                320                                     330
Lys Asp Val Cys Asp Pro Gly Asn Thr Lys Val Met Asp Lys Tyr
                                    340
Thr Phe Glu Leu Ser Arg Arg Thr His Leu Pro Glu Val Phe Leu
                350                                     360
Ser Lys Val Leu Glu Pro Thr Leu Lys Ser Leu Gly Glu Cys Cys
                                    370
Asp Val Glu Asp Ser Thr Thr Cys Phe Asn Ala Lys Gly Pro Leu
                380                                     390
Leu Lys Lys Glu Leu Ser Ser Phe Ile Asp Lys Gly Gln Glu Leu
                                    400
Cys Ala Asp Tyr Ser Glu Asn Thr Phe Thr Glu Tyr Lys Lys Lys
                410                                     420
Leu Ala Glu Arg Leu Lys Ala Lys Leu Pro Glu Ala Thr Pro Thr
                                    430
Glu Leu Ala Lys Leu Val Asn Lys Arg Ser Asp Phe Ala Ser Asn
                440                                     450
Cys Cys Ser Ile Asn Ser Pro Pro Leu Tyr Cys Asp Ser Glu Ile
                                458
Asp Ala Glu Leu Lys Asn Ile Leu
```

FIGURE 1B

```
                                        10
Leu Glu Arg Gly Arg Asp Tyr Glu Lys Asn Lys Val Cys Lys Glu
              20                                          30
Phe Ser His Leu Gly Lys Glu Asp Phe Thr Ser Leu Ser Leu Val
                  40
Leu Tyr Ser Arg Lys Phe Pro Ser Gly Thr Phe Glu Gln Val Ser
                      50                                  60
Gln Leu Val Lys Glu Val Val Ser Leu Thr Glu Ala Cys Cys Ala
                                      70
Glu Gly Ala Asp Pro Asp Cys Tyr Asp Thr Arg Thr Ser Ala Leu
                  80                                      90
Ser Ala Lys Ser Cys Glu Ser Asn Ser Pro Phe Pro Val His Pro
                                      100
Gly Thr Ala Glu Cys Cys Thr Lys Glu Gly Leu Glu Arg Lys Leu
                      110                                 120
Cys Met Ala Ala Leu Lys His Gln Pro Gln Glu Phe Pro Thr Tyr
                                  130
Val Glu Pro Thr Asn Asp Glu Ile Cys Glu Ala Phe Arg Lys Asp
                  140                                     150
Pro Lys Glu Tyr Ala Asn Gln Phe Met Trp Glu Tyr Ser Thr Asn
                                  160
Tyr Gly Gln Ala Pro Leu Ser Leu Leu Val Ser Tyr Thr Lys Ser
                  170                                     180
Tyr Leu Ser Met Val Gly Ser Cys Cys Thr Ser Ala Ser Pro Thr
                                      190
Val Cys Phe Leu Lys Glu Arg Leu Gln Leu Lys His Leu Ser Leu
                  200                                     210
Leu Thr Thr Leu Ser Asn Arg Val Cys Ser Gln Tyr Ala Ala Tyr
                                          220
Gly Glu Lys Lys Ser Arg Leu Ser Asn Leu Ile Lys Leu Ala Gln
                  230                                     240
Lys Val Pro Thr Ala Asp Leu Glu Asp Val Leu Pro Leu Ala Glu
```

(Continued in Figure 2B)

FIGURE 2A (Continued from Figure 2B)

```
                                        250
Asp Ile Thr Asn Ile Leu Ser Lys Cys Cys Glu Ser Ala Ser Glu
                260                                     270
Asp Cys Met Ala Lys Glu Leu Pro Glu His Thr Val Lys Leu Cys
                                280
Asp Asn Leu Ser Thr Lys Asn Ser Lys Phe Glu Asp Cys Cys Gln
                290                                     300
Glu Lys Thr Ala Met Asp Val Phe Val Cys Thr Tyr Phe Met Pro
                                310
Ala Ala Gln Leu Pro Glu Leu Pro Asp Val Glu Leu Pro Thr Asn
                320                                     330
Lys Asp Val Cys Asp Pro Gly Asn Thr Lys Val Met Asp Lys Tyr
                                340
Thr Phe Glu Leu Ser Arg Arg Thr His Leu Pro Glu Val Phe Leu
                350                                     360
Ser Lys Val Leu Glu Pro Thr Leu Lys Ser Leu Gly Glu Cys Cys
                                370
Asp Val Glu Asp Ser Thr Thr Cys Phe Asn Ala Lys Gly Pro Leu
                380                                     390
Leu Lys Lys Glu Leu Ser Ser Phe Ile Asp Lys Gly Gln Glu Leu
                                400
Cys Ala Asp Tyr Ser Glu Asn Thr Phe Thr Glu Tyr Lys Lys Lys
                410                                     420
Leu Ala Glu Arg Leu Lys Ala Lys Leu Pro Asp Ala Thr Pro Lys
                                430
Glu Leu Ala Lys Leu Val Asn Lys Arg Ser Asp Phe Ala Ser Asn
                440                                     450
Cys Cys Ser Ile Asn Ser Pro Leu Tyr Cys Asp Ser Glu Ile
                                458
Asp Ala Glu Leu Lys Asn Ile Leu
```

FIGURE 2B

MACROPHAGE ACTIVATING FACTOR FROM VITAMIN D BINDING PROTEIN

This application is a continuation-in-part of application 07/767,742, filed Sep. 30, 1991, now U.S. Pat. No. 5,177,001, and a continuation in part of application 07/576,248, filed Aug. 31, 1990, now U.S. Pat. No. 5,177,002, which is a continuation in part of application 07/439,223, filed Nov. 20, 1989, abandoned.

FIELD OF THE INVENTION

The invention relates to macrophage activation, in particular to the in vitro enzymatic production of a potent macrophage activating factor.

BACKGROUND OF THE INVENTION

A. Inflammatory Response Results in Activation of Macrophages

Microbial infections of various tissues cause inflammation which results in chemotaxis and activation of phagocytes. Inflamed tissues release lysophospholipids due to activation of phospholipase A. Inflamed cancerous tissues produce alkyl-lysophospholipids and alkyl-glycerols as well as lysophospholipids, because cancerous cells contain alkylphospholipids and monoalkyl-diacylglyercols. These lysophospholipids and alkyl-glycerols, degradation products of membranous lipids in the inflamed normal and cancerous tissues, are potent macrophage activating agents (Yamamoto et al., *Cancer Res.* 47:2008, 1987; Yamamoto et al., *Cancer Immunol. Immunother.* 25:185, 1987; Yamamoto et al., *Cancer Res.* 24:6044, 1988).

Administration of lysophospholipids (5–20 $\mu$g/mouse) and alkylglycerols (10–100 ng/mouse) to mice activates macrophages to phagocytize immunoglobulin G-coated sheep red blood cells. The macrophages phagocytize the target red blood cells via their receptors recognizing the Fc portion of the immunoglobulin G but not the C3b portion of the complement (Yamamoto et al., *Cancer Res.* 47:2008, 1987).

In vitro treatment of mouse peritoneal macrophages alone with lysophospholipids or alkylglycerols results in no enhanced ingestion activity (Yamamoto et al., *Cancer Res.* 48:6044, 1988). However, incubation of peritoneal cells (mixture of macrophages and B and T lymphocytes) with lysophospholipids or alkylglycerols for 2-3 hours produces markedly enhanced Fc-receptor-mediated phagocytic activity of macrophages (Yamamoto et al., *Cancer Res.* 47:2008, 1987; Yamamoto et al., *Cancer Res.* 48: 6044, 1988).

Incubation of macrophages with lysophospholipid- or alkylglycerol-treated B and T lymphocytes in a medium containing 10% fetal calf serum developed a greatly enhanced phagocytic activity of macrophages (Yamamoto et al., *Cancer Res.* 48:6044, 1988; Homma and Yamamoto, *Clin. Exp. Immunol.* 79:307, 1990). Analysis of macrophages activating signal transmission among the nonadherent (B and T) lymphocytes has revealed that lysophospholipid- or alkylglycerol-treated B-cells can transmit a signalling factor to T-cells; in turn, the T-cells modify the factor to yield a new factor, which is capable of the ultimate activation of macrophages for ingestion capability (Yamamoto et al., *Cancer Res.* 48:6044, 1988).

B. Vitamin D-Binding Protein

Vitamin D-binding protein, also known as DBP, is an evolutionary conserved glycoprotein (Cooke and Haddad, *Endocrine Rev.* 10:294 1989). DBP from animals serologically cross-reacts with human DBP (Ogata et al., *Comp. Bioch. Physiol.* 90B:193, 1988). DBP is a genetically polymorphic plasma protein in some species and has a relative molecular weight of about 52,000. It normally constitutes about 0.5% of the plasma proteins in animals. The plasma concentration is generally about 260 $\mu$g/ml. Polymorphism of the human DBP, known as "group specific component" or "Gc protein", is demonstrable by gel electrophoretic analysis, which reveals two major phenotypes: Gc1 and Gc2 (Hirschfeld et al., *Nature* 185:931, 1960). The entire nucleotide coding sequences of the Gc1 and Gc2 genes, and the predicted amino acid sequences, have been reported (Cooke, et al., *J. Clin. Invest.* 76:2420, 1985; Yang et al., *Proc. Natl. Acad. Sci. USA* 82:7994, 1985). Gc1 is further divided into Gc1f and Gc1s subtypes which migrate electrophoretically as two bands, "fast" and "slow", (Svasti et al., *Biochem.* 18:1611, 1979).

Coopenhaver et al., *Arch. Biochem. Biophys.* 226, 218–223 (1983) reported that a post-translational glycosylation difference occurs at a threonine residue, which appeared in a region of the protein having an amino acid difference between Gc1 and Gc2.

Viau et al., *Biochem. Biophys. Res. Commun.* 117, 324–331 (1983), reported a predicted structure for the O-glucosidically linked glycan of Gc1, containing a linear arrangement of sialic acid, galactose and N-acetylgalactosamine linked to a serine or threonine residue. Polymorphism of mammalian DBP can be demonstrated by isoelectric focusing (Gahne and Juneja, *Anim. Blood Grps. Biochem. Genet.* 9:37, 1978; Van de Weghe et al., *Comp. Biochem. Physiol.* 73B:977, 1982; Ogata et al., *Comp. Biochem. Physiol.* 90B:193, 1988).

DBP may be purified by a variety of means, which have been reported in the literature. For example, DBP may be purified by 25-hydroxyvitamin $D_3$-Sepharose ® affinity chromatography from plasma of various animal species (Link, et al., *Anal. Biochem.* 157:262, 1986). DBP can also be purified by actinagarose affinity chromatography due to its specific binding capacity to actin (Haddad et al., *Biochem. J.* 218:805, 1984).

Despite the characterization and intensive study of the vitamin D-binding protein, and the existence of ready methods for its purification, the conversion of this protein to a potent macrophage activity factor has not been demonstrated until the present invention.

SUMMARY OF THE INVENTION

A process for the production of a potent macrophage activating factor is provided. Vitamin D-binding protein, which is an evolutionary conserved protein, is a precursor of the macrophage activating factor. DBP is converted to the macrophage activating factor by the action of glycosidases of B and T cells.

According to a process for preparing macrophage activating factor, DBP is contacted in vitro (i) with $\beta$-galactosidase, or (ii) with $\beta$-galactosidase in combination with sialidase, $\alpha$-mannosidase or a mixture thereof. A potent macrophage activating factor is obtained in large quantities.

According to one embodiment of the invention, DBP, which possesses an oligosaccharide moiety which includes galactose and sialic acid residues (hereinafter "DBPgs"), is contacted with β-galactosidase and sialidase to provide the macrophage activating factor. According to another embodiment, DBP which is believed to possess an oligosaccharide moiety which includes galactose and α-mannose residues (hereinafter "DBPgm") is contacted with β-galactosidase and α-mannosidase. In yet another embodiment, DBP which is believed to possess an oligosaccharide moiety which includes a galactose residue without sialic acid or α-mannose (hereinafter "DBPg") is contacted with β-galactosidase alone to form the macrophage activating factor. Because of DBP genetic polymorphism, the macrophage activating factor is preferably prepared by contacting DBP with all three enzymes to obtain the macrophage activating factor, particularly when DBP purified from pooled plasma of different individuals is utilized.

The invention also relates to a macrophage activating factor which may be prepared according to the above process or any embodiment thereof, and compositions comprising the macrophage activating factor in combination with a pharmaceutically acceptable carrier, for pharmaceutical or veterinary use.

The invention further relates to a method for inducing macrophage activation in a mammal in need thereof by administering to such mammal a macrophage activating effective amount of the novel macrophage activating factor.

"DBP" as used herein means the genetically polymorphic vitamin D-binding protein also known as "group specific component" ("Gc") in humans, including all genetic variations thereof, such as DBPg, DBPgs and DBPgm. The singular expression "DBP" is thus understood to encompass all such variants, unless stated otherwise.

By "macrophage activation" is meant the stimulation of macrophages to an increased level of phagocytic activity.

BRIEF DESCRIPTION OF THE FIGURES

FIGS. 1A and 1B contain the reported amino acid sequence of DBPgs/gm. The underlined amino acid residues at positions 152, 311, 416 and 420 differ from DBPg.

FIGS. 2A and 2B contain the reported amino acid sequence of DBPg. The underlined amino acid residues at positions 152, 311, 416 and 420 differ from DBPgs/gm.

DETAILED DESCRIPTION OF THE INVENTION

A serum factor, which has been identified as DBP, is converted to a macrophage activating factor by the action of B and T cell glycosidases. DBP exists as a polypeptide having attached thereto a specific oligosaccharide, portions of which are readily removable by treatment with readily available glycosidases. These glycosidases are equivalent to the functions of B and T cells upon the DBP. Upon treatment with specific glycosidases, DBP is unexpectedly converted to a highly potent macrophage activating factor. Thus, efficient conversion of DBP to the macrophage activating factor is achieved in vitro, in the absence of B- and T-cells. The novel macrophage activating factor formed by the enzymatic treatment of DBP is substantially pure and of such high potency that administration to a host of even a trace amount (500 picogram/kg of body weight) results in greatly enhanced phagocytic macrophage activity. Since the enzymatic generation of the novel factor bypasses the functions of B- and T-cells in macrophage activation, it has utility as a potent adjuvant for vaccination and as a post-infection therapeutic agent for serious infectious diseases.

T-cell lymphokine macrophage activating factor, also known as γ-interferon, is generated by lymphokine-producing T-cells in small amounts, or is obtained by genetic engineering. The novel macrophage activating factor of the invention, on the other hand, may be readily obtained from DBP which can be readily purified from the plasma of blood according to known purification procedures.

The polymorphic DBP phenotypes are expressed inter alia as differences in the oligosaccharide attached to the polypeptide portion of the DBP molecule. The novel macrophage activating factor of the invention may be efficiently produced from DBP by incubation with a combination of β-galactosidase and sialidase, or a combination of β-galactosidase and α-mannosidase. In some instances, treatment of DBP with β-galactosidase alone efficiently yields the macrophage activating factor. The in vitro conversion of DBP to macrophage activating factor by the action of commercially available enzymes is so efficient that an extremely high activity of macrophage activating factor is obtained.

Due to its genetic polymorphism in many mammalian species, DBP is preferably treated with all three enzymes, as an enzyme mixture. In particular, DBP obtained from pooled blood from several individuals of the species may contain more than one DBP type. Complete conversion of DBP to macrophage activating factor may thus most expeditiously be achieved by treatment with all three enzymes, as an enzyme mixture.

The molecules of the DBPgs and DBPgm penotypes on the one hand (Gc1 in humans) is believed to differ from the DBPg phenotype (Gc2 in humans) by four amino acids at positions 152, 311, 416 and 420, as reported in the literature and reproduced in FIGS. 1 and 2. The differences are as follows:

|  | 152 | 311 | 416 | 420 |
| --- | --- | --- | --- | --- |
| DBPgs, DBPgm (Gc1) | Glu | Arg | Glu | Thr |
| DBPg (Gc2) | Gly | Glu | Asp | Lys |

All three principal DBP types—DBPgm, DBPGs and DBPg—differ in the nature of the appended oligosaccharide, although it is believed that most DBP molecules having the amino acid sequence of DBPg molecules are unglycosylated. Only the glycosylated form of DBPg is a precursor for macrophage activating factor according to the process described herein. Incubation of each of DBPgm, DBPgs and DBPg molecules with galactose-specific lectin beads absorbed all three macrophage activator precursor types. Thus, the outer oligosaccharide moiety of each of the three principal human Gc types is galactose.

DBPg treated with β-galactosidase alone efficiently activates macrophages. Therefore, removal of galactose from DPBg results in the formation of the macrophage activating factor. On the other hand, two glycosidases are required to convert DBP from DBPgs and DBPgm individuals. Conversion of DBPgs to macrophage activity factor requires incubation with the combination of β-galactosidase and sialidase. DBPgm conversion requires β-galactosidase and α-mannosidase.

The innermost sugar of the oligosaccharide moiety of DBPgs and DBPgm protein is N-acetylgalactosamine (Coppenhaver et al., *Arch. Biochem. Biophys.* 226, 218-223, 1983). Treatment of these glycoproteins with endo-N-acetylglucosaminidase, which results in the cleavage of the N-acetylgalactosamine, results in a molecule which cannot be then converted to macrophage activating factor.

It is believed that DBP phenotypes and subtypes are characterized as glycoproteins having the following oligosaccharide structures linked to an amino acid residue of the protein portion of the molecule:

| DBP Type | Oligosaccharide | Representative Species |
|---|---|---|
| DBPgs | Gal—GalNAc— (with NeuNac) | human (Gc1f, Gc1s*), monkey, bovine, sheep, goat, pig, horse |
| DBPgm | Gal—GalNAc— (with αMan) | human (Gc1s, Gc1f*), bovine |
| DBPg | Gal—GalNAc— | human (Gc2), dog, cat, rat, mouse |

It is believed that the above glycosylation occurs on the protein portion of DBP through a threonine or serine residue occurring at an amino acid position corresponding to about position 420 of human DBP, or through a threonine or serine residue in the same vicinity, thus forming the O-glycosidic linkage GalNAcα(1→0)Thr or GalNAcα(1→0)-Ser. Thus, the novel macrophage activating factor comprises a protein in substantially pure form having substantially the amino acid sequence of DBP and a terminal N-acetylgalactosamine group linked to an amino acid residue in the vicinity of amino acid 420, such as Thr(418) in human DBPg (Gc2); or Thr(418) (or Thr(420)) in DBPgs/gm; or Ser(418) in those species of DBg, such as rat and mouse DBg, which contain serine at position 418 in lieu of threonine.

DBP of high purity for use in the process of the invention is most readily prepared by 25-hydroxyvitamin $D_3$-Sepharose® affinity chromatography of animal blood according to the procedure of Link et al., *Anal. Biochem.* 157, 262 (1986), the entire disclosure of which is incorporated herein by reference. DBP may also be purified by actin-agarose affinity chromatography according to the procedure of Haddad et al., *Biochem. J.* 218, 805 (1984), which takes advantage of the binding specificity of DBP for actin. The entire disclosure of Haddad et al., is incorporated herein by reference. Other methods of obtaining DBP in high purity are reported in the literature.

The glycosidases utilized in the practice of the invention are well known and commercially available. β-Galactosidase, (β-D-galactosidase galactohydrolase, EC 3.2.1.23) is obtained from *Escherichia coli.* β-Galactosidase is available, for example, from Boehringer Mannheim Biochemicals, Indianapolis, Ind., cat. no. 634395.

α-Mannosidase (α-D-mannoside mannohydrolase, EC 3.2.1.24) is obtained from the jack bean (*Canavalia ensiformis*). It is available, for example, from Boehringer Mannheim Biochemicals, cat. no. 269611.

Sialidase, also known as "neuraminidase" (acylneuraminyl hydrolase EC 3.2.1.18), is obtained from *Clostridium perfringens. Vibrio cholerae* or *Arthrobacter ureafaciens.* All three forms of sialidase are available from Boehringer Mannheim Biochemicals, cat. nos. 107590, 1080725 and 269611.

DBP is readily converted to the macrophage activating factor by contact with a hydrolytic-effective amount of one or more of the above glycosidases. Any amount of enzyme sufficient to achieve substantially complete conversion of DBP to macrophage activating factor may be utilized. About 0.1 units (1 unit being the amount of enzyme which catalyzes 1 μmole of substrate in 1 minute) of each enzyme per 1 μg of DBP is more than sufficient for this purpose. Preferably, an excess of the amount of enzyme actually necessary to convert the glycoprotein to macrophage activating factor is utilized to insure complete conversion.

The DBP and enzymes may be contacted in, for example, phosphate buffer or acetate buffer. A phosphate buffer is preferred (pH 5.5). Other media known to those skilled in the art for conducting enzymatic reactions may be substituted.

The reaction may be carried out at any temperature suitable for conducting enzymatic reactions. Typically, the temperature may vary from 25° C. to 37° C., with about 37° C. being preferred. The substrate and enzyme(s) are allowed to incubate in the reaction media until substantial conversion of DBP to macrophage activating factor is achieved. While it may be appreciated that the actual incubation times employed may depend upon several factors such as the concentration of the reactants, the reaction temperature, and the like, a reaction time of about 30 minutes at 37° C. is generally sufficient to obtain complete conversion of DBP to macrophage activating factor.

Conversion of DBP to macrophage activating factor may be conducted in any vessel suitable for enzymatic reactions. It is preferred that sialidase is utilized in insoluble form, e.g., attached to beaded agarose (Sigma Chemical Co., cat. no. N-4483), to avoid contamination of the resulting macrophage activating factor with sialidase fragments of similar molecular weight. The macrophage activating factor may be produced by adding the appropriate enzyme(s) to DBP in a liquid medium, followed by subsequent filtration of the liquid to recover the macrophage activating factor. For example, the enzyme-DBP reaction mixture may be passed through a sterilized 100 kDa cut off filter (e.g. Amicon YM 100) to remove the immobilized sialidase, β-galactosidase (MW=540 kDa) and α-mannosidase (MW=190 kDa). The filtrate contains substantially pure macrophage activating factor of high activity.

Where the conversion of large quantities of DBP to macrophage activating factor is desired, all enzymes are most advantageously contained in the solid phase. β-Galactosidase, and sialidase or α-mannosidase, most preferably a mixture of all three enzymes, is affixed to, e.g., agarose beads with a suitable coupling agent such as cyanogen bromide. Methods for attaching enzymes to solid supports are known to those skilled in the art. Conversion of DBP to macrophage activating factor by means of incubation with immobilized enzymes is preferred, as the subsequent step of separating the macrophage activating factor from the enzyme mixture is obviated.

Regardless of whether immobilized or liquid phase enzyme is utilized, it is desired to pass the product mixture through an ultrafilter, preferably a filter having a pore size no larger than about 0.45μ, to provide an aseptic preparation of macrophage activating factor.

B-cells possess the function corresponding to β-galactosidase. T-cells carry the functions corresponding to sialidase and α-mannosidase. Without wishing to be bound by any theory, it is believed that DBP is modified in vivo in an ordered sequence by the membranous enzymes of B and T lymphocytes to yield macrophage activating factor.

Activation of macrophages, which is characterized by their consequent enhanced phagocytic activity, is the first major step in a host's immune defense mechanism. Macrophage activation requires B and T lymphocyte functions, which modify DBP in a step-wise fashion, to yield the novel macrophage activating factor. Since the glycosidases used for in vitro conversion of DBP to macrophage activating factor according to the present invention correspond to the B- and the T-cell function required for production of macrophage activating factor, the in vitro enzymatic generation of the macrophage activating factor bypasses the functions of B- and T-cells. Moreover, since the herein described macrophage activating factor may be generated from blood of the same mammalian species undergoing treatment, side effects, such as immunogenicity, are believed to be minimal.

Following infection, microbial antigens are bound by macrophages. Most of this surface-bound antigen is internalized (i.e., phagocytized), and processed by digestion. The macrophages return some processed antigens to their surfaces so that antigenic determinants can be "presented" efficiently to antigen-specific lymphocytes. However, the binding, phagocytosis, processing and presentation of antigens requires that the macrophage first be activated. Development of the immune response following infection is thus typically delayed for 1-2 weeks, pending complete macrophage activation. This is the period during which B- and T-cells participate in generating the macrophage activating factor. During this lag period, the infection may become well-established.

I have observed the occurrence of macrophage activation in mice in less than six hours following administration of the macrophage activating factor prepared from DBP. Substantial antibody production is observed in mice in as little as 48 hours after coinjection of the macrophage activating factor and antigen. A large amount of antigen-specific antibody is produced within 96 hours. It is thus contemplated that the macrophage activating factor of the present invention, which is capable of inducing extemely rapid activation of macrophages, will be useful as an adjuvant for vaccination to enhance and accelerate the development of the immune response and to generate a large amount of antigen-specific antibodies. For the same reason, it is further contemplated that the macrophage activating factor will find utility as a post-infection therapeutic agent to accelerate antibody production, either alone or in combination with other therapeutic agents. This therapy should be particularly effective in treating infectious diseases with long incubating periods, such as rabies.

To minimize any possible immunologic reaction from administration of the macrophage activating factor, it is preferred that each mammalian species would receive only macrophage activating factor derived from the blood of the same species. Similarly, the risk of immunologic in individuals would be minimized by administering only the same variant of DBP-derived macrophage activating factor, in situations wherein there is intraspecies DBP polymorphism.

The macrophage activating factor may be administered to an animal to induce macrophage activation, either alone or in combination with other therapies. The amount of macrophage activating factor administered depends on a variety of factors, including the potency of the agent, the duration and degree of macrophage activation sought, the size and weight of the subject, the nature of the underlying affliction, and the like. Generally, administration of as little as about 0.5 ng of factor per kg of the subject's body weight will result in substantial macrophage activation. According to one treatment, a mammal may receive about 2 ng of macrophage activating factor per kilogram of body weight every three to five days to maintain a significant level of macrophage activation.

The macrophage activating factor may be administered by any convenient means which will result in delivery to the circulation of an amount of the factor sufficient to induce substantial macrophage activation. For example, it may be delivered by intravenous or intramuscular injection. Intramuscular administration is presently preferred as the route of administration.

The macrophage activating factor may be taken up in pharmaceutically acceptable carriers, particularly those carriers suitable for delivery of proteinaceous pharmaceuticals. The factor is soluble in water or saline solution. Thus, the preferred formulation for veterinary pharmacological use comprises a saline solution of the agent. The formulation may optionally contain other agents, such as agents to maintain osmotic balance. For example, a typical carrier for injection may comprise an aqueous solution of 0.9% NaCl or phosphate buffered saline (a 0.9% NaCl aqueous solution containing 0.01M sodium phosphate, ≈pH 7.0).

The invention is illustrated by the following non-limiting examples.

EXAMPLE 1

A. Conversion of Human DBP (Gc protein) to Macrophage Activating Factor

Gc protein (2.6 μg; Gc1 or Gc2) in 1 ml of phosphate-buffered saline (PBS-Mg) containing 0.01M sodium phosphate, 0.9% NaCl and 1 mM $MgSO_4$ was treated with 2 μl of PBS-Mg containing 0.1 U of the following enzymes or enzyme combinations.

Gclf/Gcls* conversion: sialidase (Boehringer Mannheim Biochemicals, cat. no. 107590) and β-galactosidase (Boehringer, cat. no. 634395);

Gcls conversion: α-mannosidase (Boehringer, cat. no. 107379) and β-galactosidase;

Gc2 conversion: β-galactosidase only.

The respective enzyme-Gc protein mixtures were incubated in microcentrifuge tubes for thirty minutes at 37° C. The reaction mixture containing the treated Gc protein was then diluted $10^{-4}$, $10^{-5}$ or $10^{-6}$ in 0.1% egg albumin (EA) medium, for the following assay.

B. In Vitro Assay of Macrophage Activating Factor

1. Preparation of Macrophage Tissue Culture

Peritoneal cells were collected by injecting ml of phosphate buffered saline, containing 0.01M sodium phosphate, 0.9% NaCl and 5 units/ml heparin into the peritoneal cavity of BALB/c mice. Peritoneal cells were removed and washed by low speed centrifugation and suspended in a tissue culture medium RPMI 1640 supplemented with 0.1% egg albumin (EA) medium at a concentration of $1-2 \times 10^6$ cells/ml. 1 ml aliquots of the cell suspension were layered onto 12 mm coverglasses which had been placed in the 16 mm diameter wells of tissue culture plates (Costar, Cambridge, Mass.). The plates were incubated at 37° C. in a 5% $CO_2$ incubator for 30 minutes to allow macrophage adherence to the coverglass. The coverglasses were removed, immersed with gentle agitation in RPMI medium to dislodge non-adherent B and T cells, and placed in fresh tissue culture wells containing EA-medium.

2. Preparation of Sheep Erythrocyte/Rabbit Anti-erythrocyte IgG Conjugates

Washed sheep erythrocytes were coated with subagglutinating dilutions of the purified IgG fraction of rabbit anti-sheep erythrocyte antibodies. A 0.5% suspension of rabbit IgG-coated sheep erythrocytes in RPMI 1640 medium was prepared for use in the following phagocytosis assay.

3. Phagocytosis Assay 1 ml aliquots of the diluted reaction mixture from A., above, were layered onto the macrophage-coated coverglasses from B.1., above, and incubated for 2 hours in a 5% $CO_2$ incubator at 37° c. The culture media was then removed and 0.5 ml of the 0.5% erythrocyte-IgG conjugate suspension were added to the macrophage-coated coverglasses and incubated for 1 hour at 37° C. The coverglasses were then washed in a hypotonic solution (1/5 diluted phosphate buffered saline in water) to lyse non-ingested erythrocytes. The macrophages with ingested erythrocytes were counted. The average number of erythrocytes ingested per macrophage was also determined. Macrophage phagocytic activity was calculated as an "Ingestion index"(the percentage of macrophages which ingested erythrocytes $\times$ the average number of erythrocytes ingested per macrophage). The data is set forth in Table 1 (Gc1) and Table 2 (Gc2).

TABLE 1

| Dilution of Glycosidase-Treated Gc1[1] Protein | Ingestion Index | | |
|---|---|---|---|
| | Gc1 untreated control | Gc1 treated with $\beta$-galactosidase and sialidase | Gc1 treated with $\beta$-galactosidase and $\alpha$-mannosidase |
| $10^{-4}$ | 75 ± 10 | 352 ± 15 | 295 ± 11 |
| $10^{-5}$ | 82 ± 11 | 286 ± 11 | 210 ± 8 |
| $10^{-6}$ | 79 ± 8 | 122 ± 7 | 109 ± 13 |

[1]Mixture of Gc1f and Gc1s

TABLE 2

| Dilution of Glycosidase-Treated Gc2 Protein | Ingestion Index | |
|---|---|---|
| | Gc2 Untreated control | Gc2 treated with $\beta$-galactosidase |
| $10^{-4}$ | 65 ± 13 | 325 ± 16 |
| $10^{-5}$ | 69 ± 11 | 208 ± 17 |
| $10^{-6}$ | 71 ± 20 | 116 ± 5 |

EXAMPLE 2

Conversion of Human DB (Gc Protein) to Macrophage Activating Factor with Immobilized Enzyme 1. Preparation of Immobilized Enzymes 100 mg of CNBr-activated agarose (Sepharose® 4 B) was washed with 1 mM HCl and suspended in coupling buffer (300 µl) containing NaHCO$_3$ buffer (0.1M, pH 8.3) and NaCl (0.5M). $\beta$-Galactosidase, $\alpha$-mannosidase and sialidase (2 U each enzyme) were mixed in 600 µl of the coupling buffer and incubated at room temperature for 2 hours in an end-over-end mixer. Remaining active groups in the agarose were blocked by incubation with 0.2M glycine in coupling buffer for 2 hours at room temperature. The agarose-immobilized enzyme was washed with coupling buffer to remove unabsorbed protein and glycine, followed by washing with acetate buffer (0.1M, pH 4) containing NaCl (0.5M), and additional coupling buffer. The agarose-immobilized enzyme preparations were stored at 4° C.

2. Conversion of Gc protein to Macrophage Activating Factor

Gc protein (2.6 µg; Gc1, Gc2, or mixture thereof) in 1 ml of PBS-Mg (pH 5.5) was combined with a mixture of the above-prepared agarose-immobilized enzymes (2 units each enzyme) in 1 ml of PBS-Mg (pH 5.5). The reaction mixtures were incubated in 5 ml plastic tubes at 37° C. in an end-over-end mixer for 30 minutes. The reaction mixtures were thereafter spun with a table-top centrifuge at 2,000 rpm for 15 minutes The supernatant of each reaction mixture was collected, filtered through a sterilized 0.45µ pore size filter (type HA, Millipore Company, Bedford, Mass.), and diluted.

B. In Vivo Assay of Macrophage Activating Factor

The enzymatically-modified Gc protein (40, 10, 4 and 1 picogram samples) were administered intramuscularly to BALB/c mice weighing ~20 grams. At 18 hours post-administration, peritoneal cells were collected and placed on 12 mm coverglasses in the 16 mm wells of tissue culture plates. The plates were incubated at 37° C. for 30 minutes to allow adherence of macrophages. The coverglasses were washed in RPMI 1640 medium to dislodge non-adherent cells, and then placed in new wells. Rabbit IgG-coated sheep erythrocytes as prepared in Example 1B.2. were layered onto the coverglass, and a phagocytosis assay was performed as in Example 1B.3. The results are set forth in Table 3:

TABLE 3

| Dosage of enzymatically modified Gc protein (picogram/mouse) | Ingestion Index | | | |
|---|---|---|---|---|
| | Untreated Control | | Glycosidase-treated | |
| | Gc1 | Gc1 + Gc2 | Gc1 | Gc1 + Gc2 |
| 40 | 57 ± 16 | 59 ± 7 | 322 ± 19 | 314 ± 11 |
| 10 | 55 ± 10 | 63 ± 13 | 353 ± 16 | 332 ± 14 |
| 4 | 51 ± 12 | 45 ± 8 | 163 ± 18 | 152 ± 13 |
| 1 | 63 ± 18 | 56 ± 9 | 114 ± 3 | 106 ± 5 |

EXAMPLES 3

A. Conversion of Animal DBP to Macrophage Activating Factor

Purified DBP (1.0 µg) obtained from (A) cow, (B) pooled blood of seven cows, (C) cat or (D) dog was combined with 1 ml of phosphate-buffered saline (PBS-Mg) containing 0.01M sodium phosphate, 0.9% NaCl and 1 mM MgSO$_4$ and treated with 2 µl of PBS-Mg containing 0.1 U of the enzyme combinations indicated in Table 4. The enzymes utilized were as follows:

Sialidase (Boehringer Mannheim Biochemicals, cat. no. 107590).

$\alpha$-Mannosidase (Boehringer, cat. no. 107379).

$\beta$-Galactosidase (Boehringer, cat. no. 634395)

The respective enzyme-DBP mixtures were incubated in microcentrifuge tubes for sixty minutes at 37° C. The reaction mixture containing the enzyme-treated DBP was then diluted $10^{-4}$ in 0.1% egg albumin (EA) supplemented medium, for the following assay.

B. In Vitro Assay of Macrophage Activating-Factor

1. Preparation of Macrophage Tissue Culture

Peritoneal cells were collected by injecting 5 ml of phosphate buffered saline, containing 0.01M sodium phosphate, 0.9% NaCl and 5 units/ml heparin into the peritoneal cavity of BALB/c mice. Peritoneal cells were removed and washed by low speed centrifugation and suspended in a tissue culture medium RPMI 1640 supplemented with 0.1% egg albumin (EA medium) at a concentration of $1-2 \times 10^6$ cells/ml. 1 ml aliquots of the cell suspension were layered onto 12 mm coverglasses which had been placed in the 16 mm diameter wells of tissue culture plates (Costar, Cambridge, Mass.). The plates were incubated at 37° C. in a 5% $CO_2$ incubator for 30 minutes to allow macrophage adherence to the coverglass. The coverglasses were removed, immersed with gentle agitation in RPMI medium to dislodge non-adherent B and T cells, and placed in fresh tissue culture wells containing EA-medium.

2. Preparation of Sheep Erythrocyte/Rabbit Anti-erythrocyte IgG Conjugates

Washed sheep erythrocytes were coated with subagglutinating dilutions of the purified IgG fraction of rabbit anti-sheep erythrocyte antibodies. A 0.5% suspension of rabbit IgG-coated sheep erythrocytes in RPMI 1640 medium was prepared for use in the following phagocytosis assay.

3. Phagocytosis Assay 1 ml aliquots of the diluted reaction mixture from A., above, were layered onto the macrophage-coated coverglasses from B.1., above, and incubated for 2 hours in a 5% $CO_2$ incubator at 37° C. The culture media was then removed and 0.5 ml of the 0.5% erythrocyte-IgG conjugate suspension were added to the macrophage-coated cover-glasses and incubated for 1 hour at 37° C. The coverglasses were then washed in a hypotonic solution (1/5 diluted phosphate buffered saline in water) to lyse non-ingested erythrocytes. The macrophages with ingested erythrocytes were counted. The average number of erythrocytes ingested per macrophage was also determined. Macrophage phagocytic activity was calculated as an "Ingestion index" (the percentage of macrophages which ingested erythrocytes times the average number of erythrocytes ingested per macrophage). The data are set forth in Table 4.

TABLE 4

| Glycosidases for treatment of DBP | Macrophage Activation by Glycosidase-treated DBP Ingestion Index | | | |
|---|---|---|---|---|
| | A bovine | B pooled bovine | C cat | D dog |
| — | 55 ± 10 | 67 ± 15 | 77 ± 12 | 73 ± 19 |
| Sialidase | 59 ± 15 | 71 ± 19 | 80 ± 21 | 59 ± 10 |
| β-galactosidase | 63 ± 18 | 76 ± 15 | 278 ± 35 | 284 ± 41 |
| α-Mannosidase | 61 ± 13 | 73 ± 28 | 69 ± 15 | 62 ± 26 |
| β-galactosidase + sialidase | 295 ± 34 | 335 ± 32 | 269 ± 31 | 265 ± 37 |
| α-mannosidase + sialidase | 67 ± 22 | 54 ± 12 | 73 ± 20 | 67 ± 26 |
| β-galactosidase + α-mannosidase | 72 ± 15 | 188 ± 38 | 266 ± 38 | 252 ± 33 |

It is apparent from Table 4 that bovine species display polymorphism with respect to DBP type. While the purified DBP from a single bovine individual (column A) was converted to macrophage activating factor by treatment with a combination of sialidase and β-galactosidase, treatment with β-galactosidase and either sialidase or α-mannosidase resulted in generation of macrophage activator from DBP purified from pooled bovine plasma of seven cows. It is thus apparent that the single bovine individual was of DBP type "gs" and that the pooled material was composed of DBP from both DBPgs and DBPgm individuals. Similarly, it is apparent from Table 4 that the cat and dog DBP donors were type DBPg, since treatment with galactosidase alone was sufficient for generation of macrophage activating factor.

The effect of macrophage activating factor concentration on activity was investigated by treating the same bovine DBPgs, pooled bovine DBP, and cat DBPg according to Example 3, at glycosidase-treated DBP dilutions of $10^{-4}$, $10^{-5}$ and $10^{-6}$ of the original 1.0 μg/ml solution. The results are set forth in Table 5 (bovine DBPgs), Table 6 (pooled bovine DBP) and Table 7 (cat DBPg).

TABLE 5

| Dilution of Glycosidase-Treated Bovine DBPgs | Macrophage activation by Glycosidase-treated Bovine DBPgs Ingestion Index | |
|---|---|---|
| | Bovine DBP untreated control | Bovine DBP treated with β-galactosidase and sialidase |
| $10^{-4}$ | 63 ± 12 | 289 ± 11 |
| $10^{-5}$ | 59 ± 15 | 322 ± 35 |
| $10^{-6}$ | 55 ± 18 | 116 ± 22 |

TABLE 6

| Dilution of Glycosidase-Treated pooled Bovine DBPgs and DBPgm | Macrophage Activation by Glycosidase-treated pooled bovine DBP Ingestion Index | | |
|---|---|---|---|
| | Bovine DBP untreated control | Bovine DBP treated with β-galactosidase and sialidase | Bovine DBP treated with β-galactosidase and α-mannosidase |
| $10^{-4}$ | 72 ± 25 | 312 ± 38 | 285 ± 38 |
| $10^{-5}$ | 83 ± 20 | 297 ± 45 | 203 ± 36 |
| $10^{-6}$ | 76 ± 18 | 145 ± 34 | 122 ± 23 |

TABLE 7

| Macrophage Activation by Glycosidase-treated Cat DBPg | | |
|---|---|---|
| | Ingestion Index | |
| Dilution of Glycosidase-Cat DBPg | Cat DBP untreated control | Cat DBP treated with β-galactosidase |
| $10^{-4}$ | 68 ± 26 | 320 ± 29 |
| $10^{-5}$ | 65 ± 23 | 275 ± 23 |
| $10^{-6}$ | 76 ± 20 | 108 ± 34 |

EXAMPLE 4

Purified DBP (1.0 μg from each of the species identified in Table 8, below, was treated according to Example 3 with a mixture of β-galactosidase, sialidase and α-manosidase (0.5 U each) in 1 ml of PBS-Mg containing 0.01M sodium phosphate, 0.9% NaCl and 1 mM $MgSO_4$ for sixty minutes at 37° C. The reaction mixture containing each treated DBP was then diluted $10^{-4}$ in 0.1% supplemented EA medium and assayed for macrophage activation activity according to the in vitro assay of Example 3B. The results are set forth in Table 8. It may be observed that treatment with a mixture containing all three enzymes resulted in conversion of DBP to a potent macrophage activating factor, regardless of DBP polymorphism.

TABLE 8

| | Ingestion Index | |
|---|---|---|
| Glycosidase-treated DBP | Untreated control | Treated with β-galactosidase + sialidase + α-mannosidase |
| Monkey (*Macaca fucata*) | 72 ± 26 | 295 ± 38 |
| Bovine (*Bos taurus*) | 52 ± 19 | 320 ± 52 |
| Sheep (*Ovis aries*) | 48 ± 17 | 313 ± 48 |
| Goat (*Capra hircus*) | 56 ± 24 | 289 ± 32 |
| Pig (*Sus scrofa*) | 47 ± 12 | 332 ± 27 |
| Horse (*Equus caballus*) | 69 ± 23 | 266 ± 38 |
| Cat (*Felis catus*) | 58 ± 15 | 328 ± 43 |
| Dog (*Canis familigris*) | 60 ± 17 | 337 ± 18 |
| Rat (Fisher) | 65 ± 25 | 284 ± 37 |
| Mouse (BALB/C) | 71 ± 28 | 276 ± 34 |

EXAMPLE 6

A. Conversion of DBP to Macrophage Activating Factor with Immobilized Enzyme

1. Preparation of Immobilized Enzymes 100 mg of CNBr-activated agarose (Sepharose 4B) was washed with 1mM HCl and suspended in coupling buffer (300 μl) containing $NaHCO_3$buffer (0.1M, pH 8.3) and NaCl (0.5M). β-Galactosidase, α-Mannosidase or sialidase, or a combination of all three enzymes (2 U each enzyme), were mixed in 600 μl of the coupling buffer and incubated at room temperature for 2 hours in an end-over-end mixer. Remaining active groups in the agarose were blocked by incubation with 0.2M glycine in coupling buffer for 2 hours at room temperature. The agarose-immobilized enzyme was washed with coupling buffer to remove unabsorbed protein and glycine, followed by washing with acetate buffer (0.1M, pH 4) containing NaCl (0.5M), and additional coupling buffer. The agarose-immobilized enzyme preparations were stored at 4° C.

2 Conversion of DBP to Macrophage Activating Factor

DBP in 1 ml of PBS-Mg (pH 5.5) was combined with a mixture of the above-prepared agarose-immobilized enzymes (2 units each enzyme) in 1 ml of PBS-Mg (pH 5.5). The reaction mixtures were incubated in 5 ml plastic tubes at 37° C. in an end-over-end mixer for 30 minutes. The reaction mixtures were thereafter spun with a table-top centrifuge at 2,000 rpm for 15 minutes. The supernatant of each reaction mixture was collected, filtered through a sterilized 0.45μ pore size filter (type HA, Millipore Company, Bedford, Mass.), and diluted.

B. In Vivo Assay of Macrophage Activating Factor

The enzymatically-modified DBP (100, 30, 10, 3 and 1 picogram samples) were administered intramuscularly to BALB/c mice weighing ~20 grams. At 18 hours post-administration, peritoneal cells were collected and placed on 12 mm coverglasses in the 16 mm wells of tissue culture plates. The plates were incubated at 37° C. for 30 minutes to allow adherence of macrophages. The coverglasses were washed in RPMI 1640 medium to dislodge non-adherent cells, and then placed in new wells. Rabbit IgG-coated sheep erythrocytes as prepared in Example 3B.2. were layered onto the coverglass, and a phagocytosis assay was performed as in Example 3B.3. The results are set forth in Table 9:

TABLE 9

| In Vivo Assay of Macrophage Activation by Glycosidase-treated Bovine DBPgs | | | | |
|---|---|---|---|---|
| | Ingestion Index | | | |
| | Bovine DBP | | Dog DBP | |
| Dosage of enzymatically modified DBP (picogram/mouse) | untreated control | treated with β-galactosidase and sialidase | untreated control | treated with β-galactosidase and sialidase |
| 100 | 63 ± 18 | 283 ± 42 | 55 ± 22 | 272 ± 29 |
| 30 | 56 ± 17 | 341 ± 38 | 43 ± 12 | 295 ± 35 |
| 10 | 52 ± 18 | 315 ± 44 | 63 ± 17 | 277 ± 41 |
| 3 | 51 ± 12 | 141 ± 27 | 51 ± 15 | 128 ± 27 |
| 1 | 65 ± 15 | 86 ± 12 | 60 ± 18 | 89 ± 26 |

The present invention may be embodied in other specific forms without departing from the spirit or essential attributes thereof and accordingly, reference should be made to the appended claims, rather than to the foregoing specification, as indicating the scope of the invention.

I claim:

1. A macrophage activating factor comprising an isolated and purified polypeptide having the amino acid sequence of vitamin D-binding protein, and a terminal N-acetylgalactosamine group linked to a threonine or serine residue of said polypeptide at amino acid position 418.

2. A macrophage activating factor comprising an isolated and purified polypeptide having the amino acid sequence of vitamin D-binding protein, and a terminal N-actylgalactosamine group linked to a threonine residue of said polypeptide at amino acid position 420.

3. A pharmaceutical composition comprising a macrophage activating effective amount of the macrophage activating factor of claim 1 and a pharmaceutically acceptable carrier.

4. A pharmaceutical composition comprising a macrophage activating effective amount of the macrophage activating factor of claim 2 and a pharmaceutically acceptable carrier.

* * * * *